United States Patent [19]

Cochran et al.

[11] Patent Number: 4,897,085
[45] Date of Patent: Jan. 30, 1990

[54] RECOVERY OF HYDROGEN PEROXIDE

[75] Inventors: Robert N. Cochran, West Chester; Lawrence M. Candela, Philadelphia, both of Pa.

[73] Assignee: Arco Chemical Technology, Inc., Wilmington, Del.

[21] Appl. No.: 295,411

[22] Filed: Jan. 10, 1989

[51] Int. Cl.$^4$ .................... B01D 12/00; C01B 15/026; C07C 45/00
[52] U.S. Cl. ................................ 23/293 R; 423/591; 568/320
[58] Field of Search ........................ 423/591; 568/320; 23/293 R

[56] References Cited

U.S. PATENT DOCUMENTS

| | | |
|---|---|---|
| 2,819,949 | 1/1958 | Keeler et al. . |
| 2,869,989 | 1/1959 | Keeler et al. . |
| 2,871,102 | 1/1959 | Rust et al. . |
| 2,871,103 | 1/1959 | Skinner et al. . |
| 2,871,104 | 1/1959 | Rust et al. . |
| 2,949,343 | 8/1960 | Hood et al. . |
| 3,003,853 | 10/1961 | Mecorney et al. . |
| 3,012,860 | 12/1961 | Meeker et al. . |
| 3,074,782 | 1/1963 | Meeker et al. . |
| 3,592,776 | 7/1971 | Fletcher et al. ..................... 423/591 |
| 3,714,263 | 1/1973 | Cyba .................................. 568/320 |
| 4,303,632 | 12/1981 | Gosser ................................ 423/591 |

FOREIGN PATENT DOCUMENTS

| | | | |
|---|---|---|---|
| 563196 | 9/1958 | Canada ................................ 423/591 |
| 758967 | 10/1956 | United Kingdom ................ 423/591 |
| 871830 | 7/1961 | United Kingdom ................ 423/591 |

Primary Examiner—John Doll
Assistant Examiner—Wayne A. Langel
Attorney, Agent, or Firm—William C. Long

[57] ABSTRACT

A process is provided whereby the hydrogen peroxide-containing oxidate from methyl benzyl alcohol oxidation is contacted with ethyl benzene extractive solvent and a hydrogen peroxide phase is separated from a solvent phase which also contains methyl benzyl alcohol and acetophenone.

2 Claims, 1 Drawing Sheet

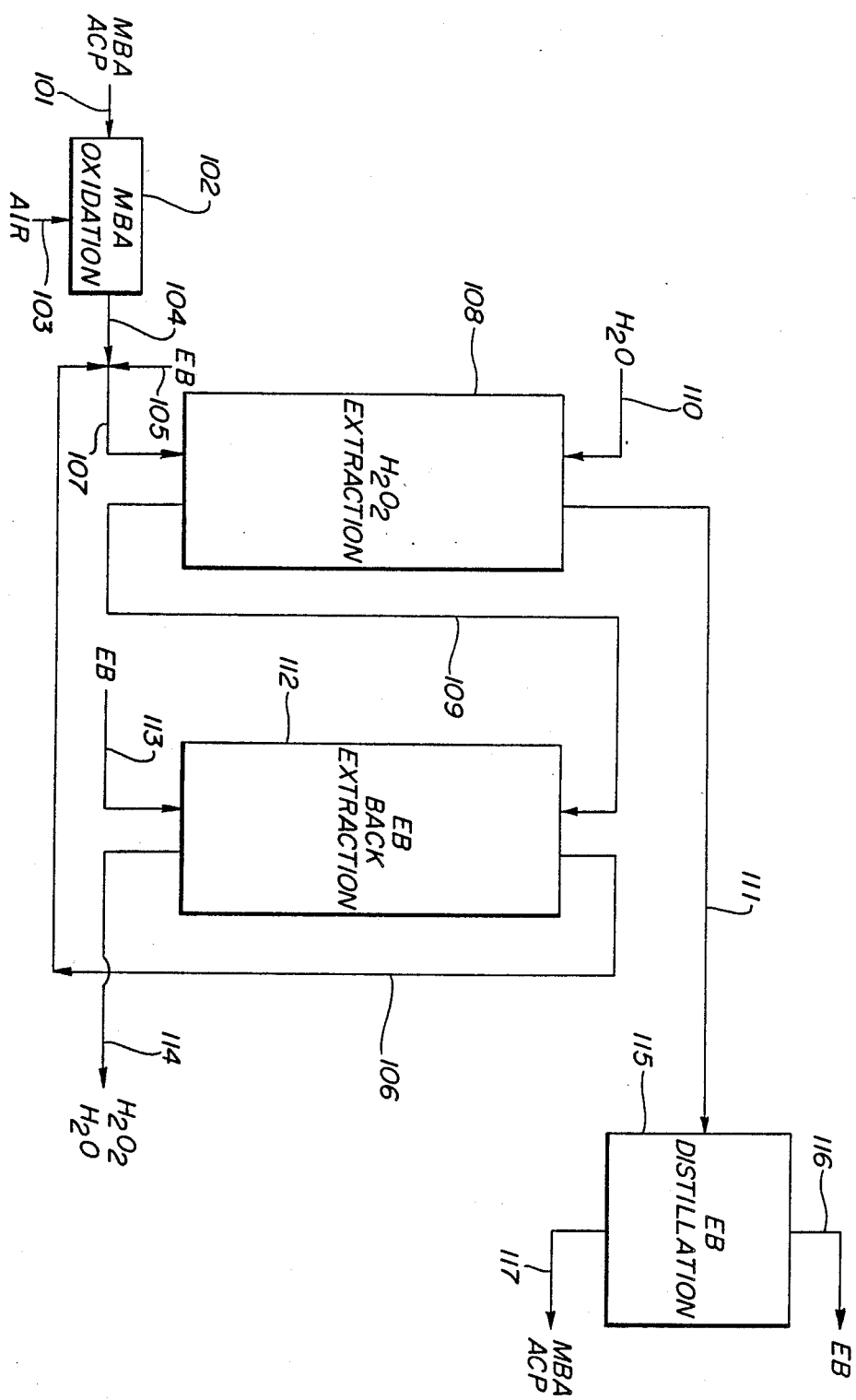

RECOVERY OF HYDROGEN PEROXIDE

BACKGROUND OF THE INVENTION

1. Field of the Invention

The present invention relates to the separation of hydrogen peroxide from methyl benzyl alcohol oxidate by ethyl benzene extraction.

2. Description of the Prior Art

Hydrogen peroxide is an important chemical of commerce which is produced in very large quantities for use in a number of industrial applications. The predominant process used commercially for the production of hydrogen peroxide involves the oxidation of anthrahydroquinone, extraction of hydrogen peroxide and reduction of the resulting anthraquinone to anthrahydroquinone which is reused. This process requires very high capital expenditures in that use of a working solvent with efficient recycle of various process components is a necessity.

Substantial efforts have been directed to processes which involve direct combination of hydrogen and oxygen but thus far such processes have not found widespread success.

Hydrogen peroxide has been formed by the oxidation of secondary alcohols. At one time the production of hydrogen peroxide by oxidation of isopropanol was practiced commercially. Other secondary alcohols which have been mentioned as starting materials for hydrogen peroxide production include methyl benzyl alcohol and cyclohexanol See, for example, U.S. Pat. Nos. 2,871,102-4 of Shell Development. In such prior procedures, difficulties have been encountered in the separation and recovery of product hydrogen peroxide from the secondary alcohol oxidate mixtures. See, for example, Shell U.S. Pat. Nos. 2,819,949, 2,869,989, 2,949,343, 3,003,853, 3,012,860 and 3,074,782.

Hydrogen peroxide has also been formed by oxidation of very high boiling secondary alcohols such as diaryl methanol, the product hydrogen peroxide being stripped from the reaction mixture during oxidation; see U.S. Pat. No. 4,303,632.

In certain commercial technologies, there are produced substantial quantities of various secondary alcohols. For example, in the coproduction of propylene oxide and styrene monomer by the reaction of ethyl benzene hydroperoxide with propylene, methyl benzyl alcohol is formed and ultimately converted by dehydration to styrene monomer. See U.S. Pat. No. 3,351,635.

In copending application filed of even date herewith, a process is described for the production of hydrogen peroxide by oxidation of methyl benzyl alcohol containing streams, such as those formed in the Oxirane process.

SUMMARY OF THE INVENTION

In accordance with the present invention there is provided an improved process for the recovery of hydrogen peroxide from methyl benzyl alcohol oxidate involving the use of ethyl benzene as an extractive solvent. Not only is efficient separation achieved, but the process is especially advantageous in that only materials normally found in the commercial propylene oxide/styrene monomer process are employed in the instant separation and recovery.

BRIEF DESCRIPTION OF THE DRAWING

The accompanying drawing illustrates in schematic form a suitable embodiment of the invention.

DETAILED DESCRIPTION OF THE INVENTION

In copending application, Ser. No. 295,409, filed of even date herewith, there is described a method for the production of hydrogen peroxide by oxidation of methyl benzyl alcohol with molecular oxygen. Acetophenone is a coproduct of the oxidation.

The present invention provides an effective method for the recovery of hydrogen peroxide from methyl benzyl alcohol oxidate reaction mixtures such as those formed in the process described in said copending application.

In accordance with the invention, the methyl benzyl alcohol oxidate mixture, which comprises methyl benzyl alcohol, acetophenone and hydrogen peroxide, is admixed with ethyl benzene extractive solvent and the resulting admixture is separated into an organic phase comprised of the ethyl benzene extractive solvent, methyl benzyl alcohol and acetophenone, and an inorganic phase comprised of hydrogen peroxide. Only about three theoretical extraction stages are needed to give essentially complete separation of hydrogen peroxide from the organic phase.

Use of ethyl benzene as the extractive solvent for recovery of hydrogen peroxide from methyl benzyl alcohol oxidate has certain unique advantages. In the first place, ethyl benzene is highly effective as the extractive solvent. Unreacted methyl benzyl alcohol as well as acetophenone are extracted into the ethyl benzene solvent while water and hydrogen peroxide are effectively excluded. In the second place, ethyl benzene is a an essential feedstock in the commercial propylene oxide/styrene monomer process which also can provide the methyl benzyl alcohol for the hydrogen peroxide production. Thus there is outstanding synergy between the technologies.

Referring to FIG. 1, a methyl benzyl alcohol stream is introduced via line 101 into oxidation reactor 102. Most suitably, the methyl benzyl alcohol stream also comprises acetophenone and represents a process stream conventionally available from propylene oxide/styrene monomer technology. Methyl benzyl alcohol is oxidized in reactor 102 by contact with molecular oxygen introduced as air via line 103. Conditions of the oxidation to form hydrogen peroxide and acetophenone are as described in said copending application Ser. No. 295,409, the contents of which are incorporated herein by reference.

Liquid reaction mixture is withdrawn from reactor 102 via line 104 and comprises unreacted methyl benzyl alcohol, acetophenone oxidation coproduct as well as such acetephenone as may be present with the methyl benzyl alcohol feed, and hydrogen peroxide product. Small amounts of water may also be present, below 4% by weight of the reaction mixture, preferably below 2% and most preferably below 1%.

Fresh ethyl benzene is introduced via line 105, and recycle ethyl benzene from ethyl benzene back extractor unit 112 is introduced via line 106 and combined with the oxidate mixture. The resulting admixture is passed to the bottom of $H_2O_2$ extractor 108. This light organic phase passes upwardly in 108, countercurrently contacting a heavy aqueous phase passing downwardly from the top, introduced by line 110. The $H_2O_2$ contained in the organic feed is extracted into the aqueous stream which exits from below via line 109.

The organic phase, now with $H_2O_2$ product removed, exits 108 from the top via line 111. This is distilled in column 115 to separate ethyl benzene overhead via line 116 from the higher boiling methyl benzyl alcohol/acetophenone mixture which is removed via line 117. The ethyl benzene can be recycled to the extraction units, or used elsewhere. The methyl benzyl alcohol/acetophenone is especially advantageously dehydrated in accordance with known procedures to form styrene monomer from the methyl benzyl alcohol, followed ultimately by hydrogenation of the acetophenone to produce more methyl benzyl alcohol The aqueous hydrogen peroxide phase removed from 108 is sent via line 109 to the top of ethyl benzene back extraction unit 112. The purpose of 112 is to remove and recover dissolved organics in stream 109 by countercurrent extraction with fresh ethyl benzene. The fresh ethyl benzene enters the bottom of extractor 112 via line 113 and travels upwards through the column. The organic product from 112 exits the top via line 106, and is recycled to the organic feed to $H_2O_2$ extractor 108. The purified aqueous hydrogen peroxide phase exits 112 via line 114 If desired, this stream can be treated by conventional procedures to further concentrate and purify the hydrogen peroxide product. The following example illustrates the invention. Unless otherwise indicated, parts are weights per hour and percentages are by weight.

EXAMPLE

A methyl benzyl alcohol oxidate in amount of 1000 parts comprised of 56.0% methyl benzyl alcohol, 37.9% acetophenone, 5.34% $H_2O_2$ and 0.7% $H_2O$ is removed from oxidizer 102 by means of line 104. To this stream is added via line 105, 531 parts of ethyl benzene and via line 106, 409 parts of an ethyl benzene recycle stream comprised of 98.0% ethyl benzene, 1.7% methyl benzyl alcohol, 0.2% acetophenone, and 0.1% $H_2O$. The admixture in amount of 1940 parts, comprised of 48.0% ethyl benzene, 29.2% methyl benzyl alcohol, 19.6% acetophenone, 2.8% $H_2O_2$ and 0.4% $H_2O$ is sent via line 107 to the bottom of $H_2O_2$ extractor 108.

To the top of 108 is sent 150 parts of a pure water stream. The $H_2O_2$ extractor has 3 theoretical stages, and operates at 20° C. and atmospheric pressure. The oraganic product from 108 is 1882 parts comprised of 49.5% ethyl benzene, 29.8% methyl benzyl alcohol, 20.1% acetophenone and 0.6% $H_2O$ and exits the top via line 111 and is sent to ethyl benzene distillation unit 112. The aqueous product from 108 is 208 parts comprised of 3.4% methyl benzyl alcohol, 0.5% acetophenone, 25.5% $H_2O_2$ and 70.6% $H_2O$ and exits the bottom via line 109.

The aqueous product from 108 is sent to the top of ethyl benzene back extractor 112. A fresh ethyl benzene stream in amount of 401 parts is sent via line 113 to the bottom of 112. This extraction column contains 5 theoretical stages, and operates at 20° C. and atmospheric pressure. The light organic product in amount of 409 parts comprised of 98% ethyl benzene, 1.7% methyl benzyl alcohol, 0.2% acetophenone and 0.1% $H_2O$ is recycled via line 106, and mixed with the organic feed to unit 108. The heavy aqueous product from 112 in amount of 199 parts comprised of 73.3% $H_2O$, 26.7% $H_2O_2$ and 230 ppm ethyl benzene+methyl benzyl alcohol+acetophenone exits via line 114. This stream can be concentrated and further purified by conventional methods.

The ethyl benzene distillation unit 115 which receives organic product from the $H_2O_2$ extractor 108 via line 111 separates ethyl benzene for recycle to the extraction units or for usage elsewhere. The overhead stream from 115 in amount of 943 parts comprised of 98.8% ethyl benzene and 1.2% $H_2O$ exits via line 116; the water can later be decanted from this stream. The bottoms product from 115 in amount of 939 parts comprised of 59.6% methyl benzyl alcohol and 40.4% acetophenone exits via line 117.

I claim:

1. The process which comprises admixing a methyl benzyl alcohol oxidate mixture containing methyl benzyl alcohol, acetophenone and hydrogen peroxide with ethyl benzene extractive solvent, and separately recovering an inorganic hydrogen peroxide phase and an organic phase containing ethyl benzene solvent, methyl benzyl alcohol and acetophenone.

2. The process of claim 1 wherein said inorganic hydrogen peroxide phase is further contacted with ethyl benzene extractive solvent to extract organic materials from said phase.

* * * * *